United States Patent [19]

D'Silva

[11] Patent Number: 5,047,550
[45] Date of Patent: Sep. 10, 1991

[54] 3-CYANO-5-HYDROXY-1-ARYLPYRAZOLES

[75] Inventors: Themistocles D. J. D'Silva, Chappel Hill, N.C.

[73] Assignee: Rhone-Poulenc AG Co., Research Triangle Park, N.C.

[21] Appl. No.: 470,172

[22] Filed: Jan. 25, 1990

Related U.S. Application Data

[62] Division of Ser. No. 317,722, Mar. 2, 1989, Pat. No. 4,918,085.

[51] Int. Cl.$^5$ .......................................... C07D 231/28
[52] U.S. Cl. .................................................. 548/365
[58] Field of Search ........................................ 548/365

[56] References Cited

U.S. PATENT DOCUMENTS 4,770,692  9/1988  Stetter et al. ............................ 71/92

FOREIGN PATENT DOCUMENTS 0249033  12/1987  European Pat. Off. .

Primary Examiner—Robert W. Ramsuer
Attorney, Agent, or Firm—Morgan & Finnegan

[57] ABSTRACT

The invention describes novel 3-cyano-4-sulfenylated-5-alkoxy-1-arylpyrazoles of general formula(I)

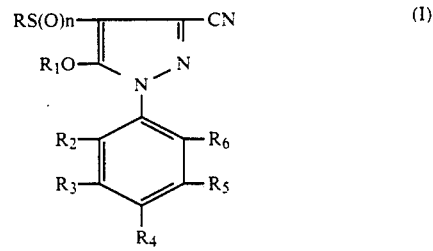

wherein typically preferred substituents are:
 R is $C_1$ to $C_4$ alkyl fully substituted by halogen;
  $R_1$ is $C_1$ to $C_4$ alkyl, $C_3$ to $C_6$ alkenyl and alkynyl or aralkyl (each of which may be optionally substituted), dialkylaminocarbonyl or a group —P(=X)(Oalkyl)(Salkyl) wherein X is oxygen or sulfur;
 $R_2$, $R_3$, $R_5$ and $R_6$ are each hydrogen or halogen;
 $R_4$ is $CF_3$, $OCF_3$, $SCF_3$, $SOCF_3$, $SO_2CF_3$, $OCHF_2$, halogen or alkyl; and
 n is 0, 1 or 2.

The invention further relates to intermediates and processes to make the compounds and to compositions thereof and to methods of control of arthopod (especially insect) nematode, helminth, and protozoan pests.

4 Claims, No Drawings

3-CYANO-5-HYDROXY-1-ARYLPYRAZOLES

This is a divisional of co-pending application Ser. No. 07/317,722 filed Mar. 2, 1989 now U.S. Pat. No. 4,918,085.

BACKGROUND OF THE INVENTION

1. Field of the Invention

This invention pertains to certain 3-cyano-4-sulfenylated-5-substituted-oxy-1-arylpyrazoles and intermediates and processes to make compounds. The invention further pertains to compositions and methods of control of arthropod, nematode, and helminth and protozoan pests and in particular to agricultural compositions and methods for controlling foliar and soil insects without causing injury to crop plants.

2. Description of the Related Art

U.S. Pat. No. 4,770,692 discloses 5-alkoxypyrazoles as herbicides and plant growth regulators. European Patent Application No. 284030 and Japanese Patent Application No. 63185965 also disclose 5-substituted-alkoxypyrazoles as herbicides. Japanese Patent application Nos. 75126663 and 75126664 disclose 5-alkoxypyrazoles as analgesic and anti-inflamatory agents. European Patent applications Nos. 234119 and 249033 disclose various pyrazoles as insecticides, acaricides, and nematicides.

SUMMARY OF THE INVENTION

The present invention provides 3-cyano-4-sulfenylated-5-substituted-oxy-1-arylpyrazoles of the general formula(I)

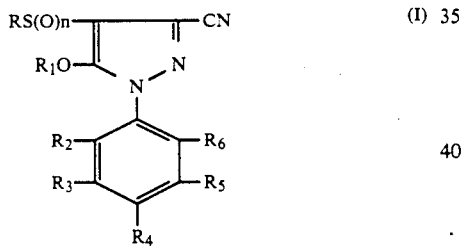

wherein:
R is selected from unsubstituted $C_1$ to $C_4$ alkyl or $C_1$ to $C_4$ alkyl substituted by one or more halogen atoms, which are the same or different, up to full substitution;
$R_1$ is selected from $C_1$ to $C_4$ alkyl, $C_3$ to $C_6$ alkenyl, $C_3$ to $C_6$ alkynyl, aralkyl or aryl, wherein $R_1$ is unsubstituted or substituted by one or more groups selected from halogen, alkyl, nitro, alkoxy, alkylthio, alkylsulfinyl, alkylsulfonyl, hydroxy, cyano, carboxy, alkoxycarbonyl, aminocarbonyl, alkylaminocarbonyl or dialkylaminocarbonyl, or $R_1$ is selected from aminocarbonyl, alkylaminocarbonyl or dialkylaminocarbonyl, wherein the defined alkyl and alkoxy moieties of the $R_1$ groups each contain one to four carbon atoms, or $R_1$ is $-P(=X)OR_7SR_8$ wherein X is an oxygen atom or a sulfur atom;
$R_2$, $R_3$, $R_5$ and $R_6$ are individually a hydrogen atom or a halogen atom;
$R_4$ is selected from a halogen atom or a $C_1$ to $C_4$ straight chain or branched chain alkyl, alkoxy, alkylthio, alkylsulfinyl or alkylsulfonyl group, which group is unsubstituted or substituted by one or more halogen atoms which are the same or different;
$R_7$ is methyl or ethyl;
$R_8$ is straight chain or branched chain $C_3$ to $C_4$ alkyl; and
n is 0, 1 or 2.

According to a preferred feature of the invention, the pesticidal compounds are selected from amongst the compounds of the formula (II)

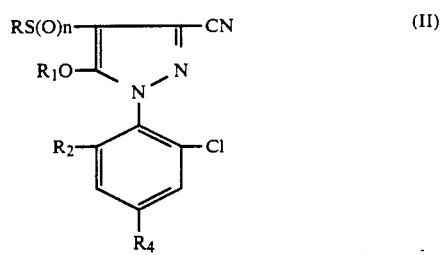

wherein:
R is $C_1$ to $C_4$ alkyl fully substituted by halogen atoms which are the same or different;
$R_1$ is selected from $C_1$ to $C_4$ alkyl, $C_3$ to $C_6$ alkenyl, $C_3$ to $C_6$ alkynyl or aralkyl, wherein $R_1$ is unsubstituted or substituted by one or more groups selected from halogen, alkyl, cyano, alkoxycarbonyl or dialkylaminocarbonyl, or $R_1$ is selected from dialkylaminocarbonyl, wherein the defined alkyl and alkoxy moieties of the $R_1$ groups each contain one to four carbon atoms, or $R_1$ is $-P(=X)OR_7SR_8$ wherein X is an oxygen atom or a sulfur atom;
$R_2$ is a hydrogen atom or a halogen atom;
$R_4$ is selected from a halogen atom, $CF_3$, $OCF_3$, $SCF_3$, $SOCF_3$, $SO_2CF_3$, $OCHF_2$ or $C_1$ to $C_4$ alkyl;
$R_7$ is methyl or ethyl;
$R_8$ is straight chain or branched chain $C_3$ to $C_4$ alkyl; and
n is 0, 1 or 2.

It is an objective of the present invention to provide new compounds of the pyrazole family together with processes for their preparation and intermediates thereto.

A second objective of the present invention is to provide, for example, agronomically and medicinally acceptable compositions.

A third objective of the present invention is to provide highly active compounds for use against arthropods, especially insects, plant nematodes, and helminth and protozoan pests. The compounds are thus advantageously used, for example, in agricultural and horticultural crops, forestry, veterinary medicine and livestock husbandry, and in public health.

A further objective of the present invention is to provide compounds with broad spectrum activity as insecticides, miticides, and nematicides, by either soil or foliar application.

An additional objective of the present invention is to provide compounds which are especially highly active on soil dwelling insects (e.g., corn rootworm species) and Dipteran (fly) species.

These and other objectives of the invention are totally or partially obtained with the new compounds herein defined.

DESCRIPTION OF SPECIFIC EMBODIMENTS

PROCESSES AND REPRESENTATIVE COMPOUNDS OF THE INVENTION

The 3-cyano-4-sulfenylated-5-alkoxy-1-arylpyrazoles of this invention can be conveniently prepared by a variety of methods. Two preferred methods are illustrated by reaction SCHEMES I and II, in which R' is a $C_1$ to $C_4$ alkyl group and R, $R_1$ to $R_8$ and n are as previously defined.

SCHEME I

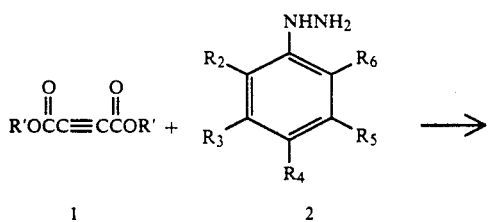

1        2

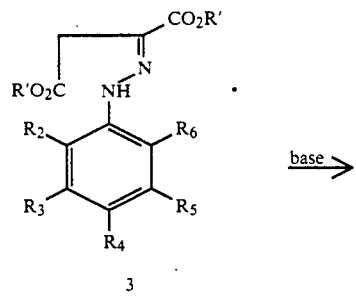

3

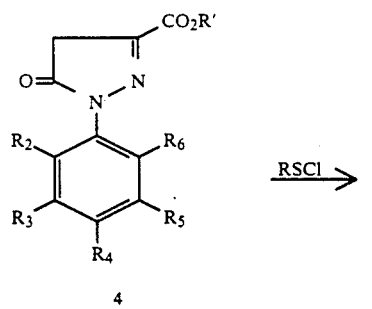

4

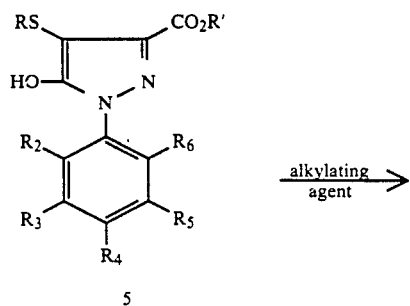

5

-continued
SCHEME I

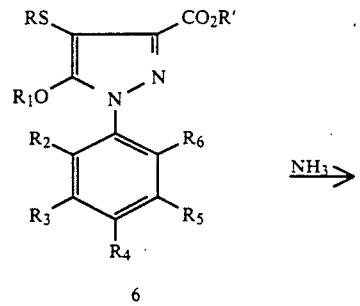

6

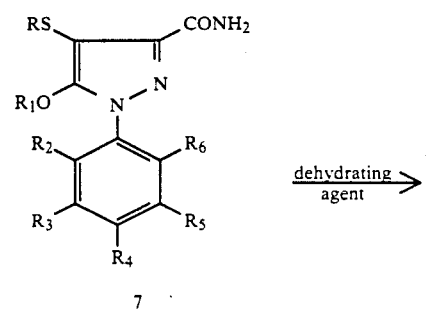

7

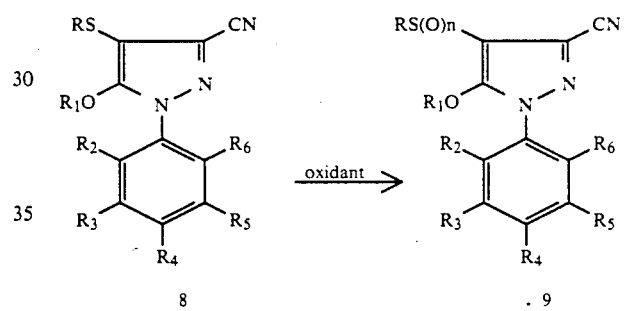

8        9

In Scheme I the starting materials, the acetylene dicarboxylates 1 are commercially available and the phenylhydrazines 2 are also commercial products or may be prepared following well known literature procedures. The intermediate hydrazones 3 may be isolated or cyclized to 4 without isolation by treating with a base, such as a tertiary amine, hydroxide, an alkoxide or a carbonate of alkali or alkaline earth metals. The reaction may be carried out between $-80°$ to $150°$ C., preferably $0°$ to $40°$ C. Alternatively, pyrazolones of the type 4 may also be prepared by the method described in British Patent Specification No. 585,780, incorporated herein by reference.

The reaction of pyrazolones 4 with sulfenyl chlorides may be conveniently conducted in aprotic solvents such as chlorinated hydrocarbons, hydrocarbons, ethers, etc., preferably in dichloromethane, using an acid acceptor such as pyridine or any tertiary amine. The reaction may be carried out between about $-20°$ and about $100°$ C. depending on the boiling point of the sulfenyl halide reagent and solvent.

The hydroxy pyrazoles 5 may be alkylated to the corresponding ether 6 by reacting with dialkyl sulfates, such as dimethyl sulfate or diethyl sulfate or with an alkyl halide, such as methyl iodide, methyl bromide, ethyl iodide or bromide and the like using any of the bases described previously. The reaction is usually conducted in an inert organic solvent, typically at reflux temperature in the range of about 30° C. to about 180° C.

In a similar manner, benzyl halides, alkenyl halides and alkynyl halides may also be used to prepare the corresponding benzyl ethers, alkenyl ethers and alkynyl ethers. Alternatively, the methyl ethers 6 may also be prepared by reacting 5 with diazomethane in an ether solvent. The pyrazolones 5 may also be reacted with an alpha-haloester or an alpha-haloketone in the presence of a base to prepare ethers with an ester or carbonyl functionality.

The carboxamide 7 may be prepared by reacting the ester 6 in an inert organic solvent with ammonia under pressure at ambient temperature. Alternatively, 6 may be hydrolyzed to the corresponding acid and converted to the acid chloride by well known chemistry. This can then be further reacted with ammonia to afford the carboxamide 7.

The dehydration of the carboxamide 7 to the nitrile 8 may be carried out using standard dehydrating agents, such as phosphorous oxychloride or phosphorous pentoxide, without or with an inert organic solvent, and usually at the reflux temperature of the solvent which is typically between about 30° C. to about 180° C. Usual preferred solvents are aliphatic or aromatic hydrocarbons, chlorinated hydrocarbons, and ethers.

The oxidation of the sulfides 8 to the sulfoxides or sulfones 9 may be carried out by using appropriate quantities of peracetic acid or trifluoroperacetic acid or m-chloroperbenzoic acid or hydrogen peroxide or a combination of peracetic acid and hydrogen peroxide or potassium peroxymonosulfate which is commercially available as Oxone®. The reaction is usually conducted in an inert organic solvent, typically in the range of about −30° C. to about 180° C.

For SCHEME II the preparation of intermediates 10 and pyrazolones of the type 13 are described in British Patent Specification No. 585780, European Patent Application No. 265305 and Japanese Patent No. 75116473, incorporated herein by reference.

The conditions used in the sulfenylation of 13 to 14 and alkylation of 14 to 8 are similar to the ranges of the reaction parameters described for related compounds, i.e., compounds of formulae 4 to give 5 and 5 to give 6, respectively, prepared according to SCHEME I.

The hydrazones 12 may exist as mixtures of geometric isomers and the pyrazolones 13 may also exist in their tautomeric forms 13a and 13b. All the isomers are within the scope of this invention.

SCHEME II

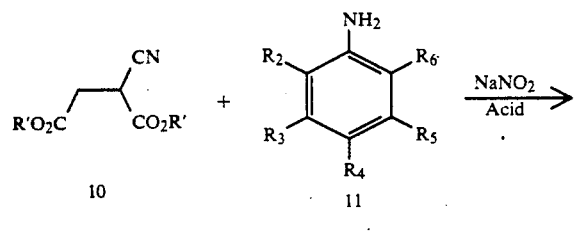

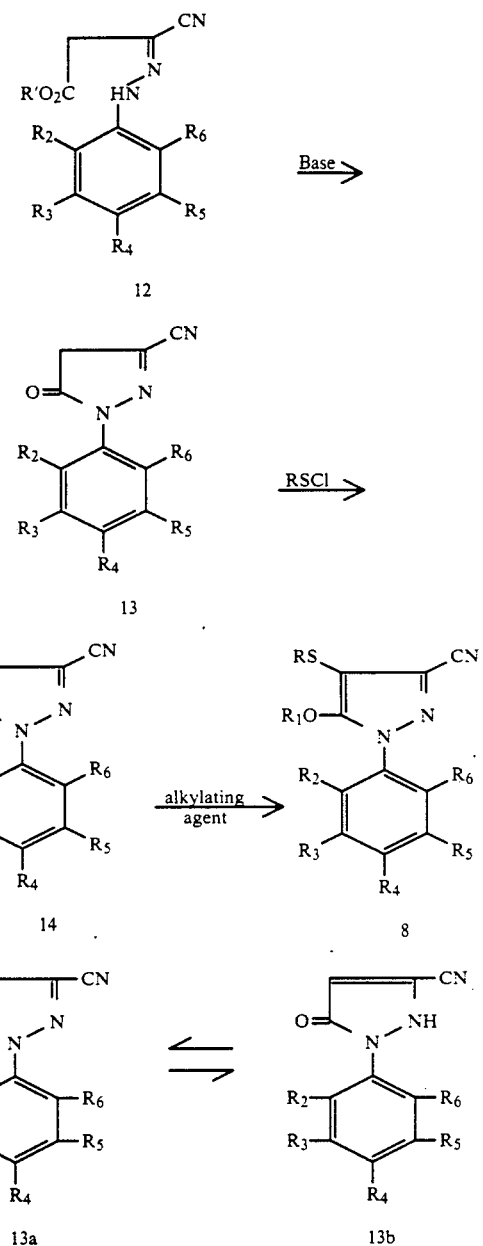

Representative non-limiting compounds which are contemplated and typically preferred by the invention are compounds of the general formula(I), wherein the substituents have the meanings described in TABLE 1.

TABLE 1

REPRESENTATIVE 1-ARYLPYRAZOLE COMPOUNDS OF FORMULA (I)
SUBSTITUENT GROUPS

| R | n | $R_1$ | $R_2$ | $R_3$ | $R_4$ | $R_5$ | $R_6$ |
|---|---|---|---|---|---|---|---|
| $CF_3$ | 0 | $CH_3$ | Cl | H | $CF_3O$ | H | Cl |
| $CF_3$ | 0 | $C_2H_5$ | Cl | H | $CF_3O$ | H | Cl |
| $CF_3$ | 0 | $(CH_3)_2CH$ | Cl | H | $CF_3$ | H | Cl |
| $CF_3$ | 1 | $CH_3$ | Cl | H | $CF_3O$ | H | Cl |

TABLE 1-continued

REPRESENTATIVE 1-ARYLPYRAZOLE COMPOUNDS OF FORMULA (I)
SUBSTITUENT GROUPS

| R | n | $R_1$ | $R_2$ | $R_3$ | $R_4$ | $R_5$ | $R_6$ |
|---|---|-------|-------|-------|-------|-------|-------|
| $CF_3$ | 2 | $CH_3$ | Cl | H | $CF_3O$ | H | Cl |
| $CF_3$ | 0 | $CH_3$ | Cl | H | Cl | H | Cl |
| $CF_3$ | 1 | $CH_3$ | Cl | H | Cl | H | Cl |
| $CF_3$ | 2 | $CH_3$ | Cl | H | Cl | H | Cl |
| $CF_3$ | 0 | $CH_3$ | H | H | $CF_3$ | H | Cl |
| $CF_3$ | 0 | $C_2H_5$ | H | H | $CF_3$ | H | Cl |
| $CF_3$ | 0 | $CH_3$ | Br | H | $CF_3$ | H | Cl |
| $CF_3$ | 0 | $C_2H_5$ | Br | H | $CF_3$ | H | Cl |
| $CF_3$ | 1 | $CH_3$ | H | H | $CF_3$ | H | Cl |
| $CF_3$ | 0 | $CH_3$ | H | H | $CF_3O$ | H | Cl |
| $CF_3$ | 0 | $CH_3$ | Cl | H | $CF_3O$ | H | Cl |
| $CF_3$ | 1 | $CH_3$ | Cl | H | $CF_3SO$ | H | Cl |
| $CF_3$ | 2 | $CH_3$ | Cl | H | $CF_3SO_2$ | H | Cl |
| $CF_3$ | 0 | $CH_3$ | Cl | H | $CF_3SO$ | H | Cl |
| $CF_3$ | 0 | $CH_3$ | Cl | H | $CF_3SO_2$ | H | Cl |
| $CF_3$ | 1 | $CH_3$ | Cl | H | $CF_3SO_2$ | H | Cl |
| $CFCl_2$ | 0 | $CH_3$ | Cl | H | $CF_3O$ | H | Cl |
| $CH_3$ | 0 | $CH_3$ | Cl | H | $CF_3$ | H | Cl |
| $CH_3$ | 1 | $CH_3$ | Cl | H | $CF_3$ | H | Cl |
| $CH_3$ | 2 | $CH_3$ | Cl | H | $CF_3$ | H | Cl |
| $CF_3$ | 0 | $NCCH_2$ | Cl | H | $CF_3$ | H | Cl |
| $CF_3$ | 0 | $CH_3SO_2CH_2$ | Cl | H | $CF_3$ | H | Cl |
| $CF_3$ | 1 | $NCCH_2$ | Cl | H | $CF_3$ | H | Cl |
| $CF_3$ | 0 | $PhCH_2$ | Cl | H | $CF_3$ | H | Cl |
| $CFCl_2$ | 0 | $HC{\equiv}C{-}CH_2$ | Cl | H | $CF_3$ | H | Cl |
| $CFCl_2$ | 1 | $HC{\equiv}C{-}CH_2$ | Cl | H | $CF_3$ | H | Cl |
| $CF_3$ | 0 | $HC{\equiv}C{-}CH_2$ | Cl | H | $CF_3$ | H | Cl |
| $CF_3$ | 1 | $HC{\equiv}C{-}CH_2$ | Cl | H | $CF_3$ | H | Cl |
| $CF_3$ | 0 | $H_2C{=}CH{-}CH_2$ | Cl | H | $CF_3$ | H | Cl |
| $CF_3$ | 2 | $HC{\equiv}C{-}CH_2$ | Cl | H | $CF_3$ | H | Cl |
| $CFCl_2$ | 0 | $H_2C{=}CH{-}CH_2$ | Cl | H | $CF_3$ | H | Cl |
| $CF_3$ | 0 | $NCCH_2CH_2$ | Cl | H | $CF_3$ | H | Cl |
| $CF_3$ | 1 | $NCCH_2CH_2$ | Cl | H | $CF_3$ | H | Cl |
| $CF_3$ | 0 | $HOCH_2CH_2$ | Cl | H | $CF_3$ | H | Cl |
| $CF_3$ | 0 | $CH_3O_2CCH_2$ | Cl | H | $CF_3$ | H | Cl |
| $CF_3$ | 1 | $CH_3O_2CCH_2$ | Cl | H | $CF_3$ | H | Cl |
| $CF_3$ | 2 | $CH_3O_2CCH_2$ | Cl | H | $CF_3$ | H | Cl |
| $CFCl_2$ | 0 | $C_2H_5O_2CCH_2$ | Cl | H | $CF_3$ | H | Cl |
| $CF_2Cl$ | 0 | $C_2H_5O_2CCH_2$ | Cl | H | $CF_3$ | H | Cl |
| $CF_3$ | 0 | $(CH_3)_2NOCCH_2$ | Cl | H | $CF_3$ | H | Cl |
| $CF_3$ | 1 | $(CH_3)_2NOCCH_2$ | Cl | H | $CF_3$ | H | Cl |
| $CF_3$ | 0 | $CH_3O_2CCH(CH_3)$ | Cl | H | $CF_3$ | H | Cl |
| $CF_3$ | 1 | $CH_3O_2CCH(CH_3)$ | Cl | H | $CF_3$ | H | Cl |
| $CF_3$ | 2 | $CH_3O_2CCH(CH_3)$ | Cl | H | $CF_3$ | H | Cl |
| $CF_3$ | 0 | $CH_3O_2CCH_2CH_2$ | Cl | H | $CF_3$ | H | Cl |
| $CF_3$ | 0 | $ClCH_2C(OCH_3)CH_2$ | Cl | H | $CF_3$ | H | Cl |
| $CF_3$ | 0 | $CH_3$ | F | F | $CF_3$ | F | F |
| $CF_3$ | 1 | $CH_3$ | F | F | $CF_3$ | F | F |
| $CF_3$ | 2 | $CH_3$ | F | F | $CF_3$ | F | F |
| $CFCl_2$ | 0 | $CH_3$ | F | F | $CF_3$ | F | F |
| $CFCl_2$ | 1 | $CH_3$ | F | F | $CF_3$ | F | F |
| $CFCl_2$ | 2 | $C_2H_5$ | F | F | $CF_3$ | F | F |
| $CF_3$ | 1 | $CH_3SO_2CH_2$ | Cl | H | $CF_3$ | H | Cl |
| $CF_3$ | 2 | $CH_3SO_2CH_2$ | Cl | H | $CF_3$ | H | Cl |
| $CF_3$ | 2 | $NCCH_2$ | Cl | H | $CF_3$ | H | Cl |
| $CF_3$ | 0 | $CH_3NHCOCH(CH_3)$ | Cl | H | $CF_3$ | H | Cl |
| $CF_3$ | 1 | $CH_3NHOCCH(CH_3)$ | Cl | H | $CF_3$ | H | Cl |
| $CF_3$ | 0 | $C_2H_5NHOCCH(CH_3)$ | Cl | H | $CF_3$ | H | Cl |
| $CF_3$ | 0 | $CH_3NHCOCH(CH_3)$ | Cl | H | $CF_3$ | H | F |
| $CFCl_2CF_2$ | 0 | $CH_3$ | Cl | H | $CF_3$ | H | Cl |
| $CFCl_2CF_2$ | 1 | $CH_3$ | Cl | H | $CF_3$ | H | Cl |
| $CFCl_2CF_2$ | 2 | $CH_3$ | Cl | H | $CF_3$ | H | Cl |
| $CF_3$ | 0 | $(C_2H_5O)(sBuS)P(O)$ | Cl | H | $CF_3$ | H | Cl |
| $CF_3$ | 0 | $(CH_3)_2NOC$ | Cl | H | $CF_3$ | H | Cl |
| $CFCl_2$ | 0 | $(CH_3)_2NOC$ | Cl | H | $CF_3$ | H | Cl |
| $CF_3$ | 0 | $CH_3SCH_2$ | Cl | H | $CF_3$ | H | Cl |
| $CF_3$ | 0 | $C_2H_5$ | Cl | H | $CF_3$ | H | Cl |
| $CF_3$ | 0 | $CH_3$ | Cl | H | $t\text{-}C_4H_9$ | H | Cl |

The following examples illustrate the preparation of preferred typical and representative compounds of formula (I) and (II) of this invention and the intermediates and processes thereto.

Preparation of
1-(2,6-dichloro-4-trifluoromethylphenyl)-3-cyano-4-tri-
fluoromethylsulfenyl-5-methoxypyrazole Process SCHEME I a) Preparation of intermediate:
1-(2,6-dichloro-4-trifluoromethylphenyl)-3-(methox-
ycarbonyl)-pyrazol-5-one To a solution of 30.1 g (0.123 mole) of 2,6-dichloro-4-trifluoromethylphenylhydrazine in 75 ml of methanol was added dropwise with stirring a solution of 18.5 g (0.13 mole) of dimethylacetylene dicarboxylate dissolved in 75 ml of methanol. The reaction mixture was stirred for 2.5 hrs. at 10°–20° C. The brown mixture was then added slowly, over a period of 50 min., to a stirred solution of sodium methoxide (made by dissolving 11.0 g (0.478 mole) of sodium in 400 ml of anhydrous methanol). After stirring for an additional period of 1.5 hr, the solution was concentrated under a partial vacuum and acidified with 100 ml of 4N hydrochloric acid. The precipitated solid was filtered, washed with water and air dried to afford 28.4 g (65 percent yield) of a tan colored solid, mp 245°–246° C., which was recrystallized from methanol to give a solid, mp 249°–250° C.

b) Preparation of intermediate:
1-(2,6-dichloro-4-trifluoromethylphenyl)-3-methox-
ycarbonyl-4-trifluoromethylsulfenyl-5-hydrox-
ypyrazole To a solution of 10 g (0.028 mole) of 1-(2,6-dichloro-4-trifluoromethylphenyl)-3-(methoxycarbonyl)-pyrazol-5-one in 150 ml of dichloromethane containing 2.45 g (0.03 mole) of pyridine, cooled to −10° to 0° C., was added 3.75 ml (0.04 mole) of trifluoromethanesulfenyl chloride. The reaction mixture was allowed to stir overnight, then diluted with ethyl acetate and washed with water. The organic layer was dried and concentrated to afford 13.0 g of a tan colored solid. Recrystallization from hexane:methyl-t-butyl ether afforded 5.5 g of a product, m.p. 216.5°–217.5° C.
Calculated for $C_{13}H_6Cl_2F_3N_2O_3S$: C, 34.30; H, 1.32; N, 6.15. Found: C, 34.43; H, 1.46; N, 6.01.

c) Preparation of intermediate:
1-(2,6-dichloro-4-trifluoromethylphenyl)-3-methox-
ycarbonyl-4-trifluoromethylsulfenyl-5-methox-
ypyrazole A suspension of 5.8 g (0.013 mole) of 1-(2,6-dichloro-4-trifluoromethylphenyl)-3-methoxycarbonyl-4-trifluoromethylsulfenyl-5-hydroxypyrazole and 0.37 g (0.015 mole) sodium hydride in 150 ml of dioxane was heated to reflux for 0.5 hr. during which time the color changed from brown to orange with evolution of gas. To the cooled mixture was added 1.94 g (0.015 mole) of dimethyl sulfate diluted in 10 ml of dioxane. The mixture was heated again to reflux for 1 hr. It was then cooled, the solids were filtered off and the filtrate was concentrated. The brown oil was taken up in dichloromethane and washed with water. The organic layer was dried and concentrated to afford 3.8 g (62.4 percent yield) of a brown oil. Purification by column chromatography using silica gel gave a solid, m.p. 97°–98° C.
Calculated for $C_{14}H_8Cl_2F_6N_2O_3S$: C, 35.83; H, 1.70; N, 5.97. Found: C, 36.40; H, 1.75; N, 5.86.

d) Preparation of intermediate:
1-(2,6-dichloro-4-trifluoromethylphenyl)-3-aminocar-
bonyl-4-trifluoromethylsulfenyl-5-methoxypyrazole Ammonia gas was bubbled into a pressure bottle containing a cooled solution of 3.5 g of 1-(2,6-dichloro-4-trifluoromethylphenyl)-3-methoxycarbonyl-4-trifluoromethylsulfenyl-5-methoxypyrazole in 100 ml of methanol so as to obtain a saturated solution. The bottle was sealed and left standing at ambient temperature and an initial pressure of 6 to 10 p.s.i.g. After 16 hrs., the reaction mixture was concentrated under partial vacuum. After chromatographic purification, there was obtained 2.86 g (84 percent yield) of a solid, m.p. 149.5°–151° C.
Calculated for $C_{13}H_7Cl_2F_6N_3O_2S$: C, 34.37; H, 1.55; N, 9.25. Found: C, 34.58; H, 1.78; N, 9.05.

e) Preparation of
1-(2,6-dichloro-4-trifluoromethylphenyl)-3-cyano-4-tri-
fluoromethylsulfenyl-5-methoxypyrazole A mixture of 3.5 g of 1-(2,6-dichloro-4-trifluoromethyl)-3-aminocarbonyl-4-trifluoromethylsulfenyl-5-methoxypyrazole in 25 ml of phosphorous oxychloride was heated under reflux for 2 hrs. On cooling, the mixture was slowly poured into 200 ml of ice. The yellow precipitate was filtered and dissolved in ethyl acetate. The organic layer was dried and concentrated. Crystallization from hexane and isopropanol afforded 2.88 g (85.7 percent yield) of a white solid, m.p. 83°–84.5° C.
Calculated for $C_{13}H_5Cl_2F_6N_3OS$: C, 35.72; H, 1.15; N, 9.63. Found: C, 36.11; H, 1.44; N, 9.46.

Process SCHEME II f) Preparation of intermediate: ethyl
3-cyano-3-(2,6-dichloro-4-trifluoromethylphenyl)hy-
drazonopropionate Preparation of the diazonium salt:
Sodium nitrite (6.27 g, 0.0909 mole) was added in three portions to stirred conc. sulfuric acid (58.3 g, 0.595 mole). The mixture was kept cold by external cooling with ice. The sulfuric acid-sodium nitrite mixture was heated to 80° C. until all the solid had dissolved, forming a clear yellow solution. The nitrosylsulfuric mixture was cooled to room temperature and diluted with 57 ml of glacial acetic acid. To this mixture was added, with stirring, a solution of 19.0 g (0.0826 mole) 2,6-dichloro-4-trifluoromethylaniline dissolved in 50 ml of acetic acid. The mixture was heated to 50°–65° C. for 1 hour and cooled.

Reaction of the diazonium salt with diethyl cyanosuccinate:

The diazonium salt, prepared as in EXAMPLE 1f was added dropwise to a stirred solution of 14.7 g (0.0859 mole) of diethyl cyanosuccinate dissolved in 115 ml of acetic acid and 170 ml of water. After the addition was completed, a solution of 115 g of sodium acetate in 200 ml of water was added to the reaction mixture and stirring was continued for 0.5 h. The reaction was then poured into 1000 ml of ice and water. The aqueous mixture was extracted four times with 300 ml portions of dichloromethane and the combined organic extracts were washed with 230 ml of ammonium hydroxide. The aqueous extract was discarded. The organic layer was stirred overnight with an additional 460 ml of ammonium hydroxide. The organic phase was separated, dried and concentrated to afford 19.5 g of an orange colored oil. Chromatographic purification afforded 11.4 g of a solid as a mixture of geometric isomers as analyzed by NMR. A mass spectral analysis gave m/e=368 (M+).

Calculated for $C_{13}H_{10}Cl_2F_3N_3O_2$: C, 42.11; H, 2.73; N, 11.41. Found: C, 42.02; H, 2.63; N, 11.26.

g) Preparation of intermediate: 1-(2,6-Dichloro-4-trifluoromethylphenyl)-3-cyanopyrazol-5-one A solution of 1.0 g (0.0027 mole) of the hydrazone (prepared as in EXAMPLE 1f) in 25 ml of anhydrous ethanol was added dropwise to a solution of sodium ethoxide (prepared by dissolving 0.23 g (0.01 mole) of sodium metal in 75 ml of anhydrous ethanol). After stirring for 3 hrs. at room temperature, the ethanol was removed under reduced pressure and the residue was dissolved in water, cooled and acidified with 4N hydrochloric acid to pH 1. The oily mixture was extracted with dichloromethane. The solution was dried and concentrated to afford 0.87 g of the desired product. Crystallization from toluene gave a tan solid which melted at 198°–201° C.

h) Preparation of intermediate: 1-(2,6-Dichloro-4-trifluoromethylphenyl)-3-cyano-4-trifluoromethylsulfenyl-5-hydroxypyrazole To a solution of 0.25 g (0.78 mmole) of 1-(2,6-dichloro-4-trifluoromethylphenyl)-3-cyanopyrazol-5-one in 15 ml of dichloromethane and 0.069 ml (0.86 mmole) of pyridine, cooled to −70° C. and kept under nitrogen, was added 0.1 ml (1.0 mmole) of trifluoromethanesulfenyl chloride. After stirring for 3 hrs., the reaction was allowed to warm to ambient temperature. The excess of trifluoromethanesulfenyl chloride was removed and the reaction mixture was diluted with ethyl acetate, washed with water, dried and concentrated to an orange colored oil. Chromatographic purification afforded 0.04 g of white solid, m.p. 325° C. (decomp.).

i) Preparation of 1-(2,6-dichloro-4-trifluoromethylphenyl)-3-cyano-4-trifluoromethylsulfenyl-5-methoxypyrazole Methylation of 1-(2,6-dichloro-4-trifluoromethylphenyl)-3-cyano-4-trifluoromethylsulfenyl)-5-hydroxypyrazole with dimethyl sulfate was carried out according to the procedure described in EXAMPLE 1c. The product was identical to that produced in EXAMPLE 1e.

EXAMPLE 2

Preparation of 1-(2,6-dichloro-4-trifluoromethylphenyl)-3-cyano-4-trifluoromethylsulfonyl-5-methoxypyrazole To a solution of 1.57 g (0.0036 mole) of 1-(2,6-dichloro-4-trifluoromethylphenyl)-3-cyano-4-trifluoromethylsulfenyl-5-methoxypyrazole in 50 ml chloroform was added 1.36 g (0.0079 mole) of m-chloroperbenzoic acid. The solution was heated under reflux 3 days. The solid which precipitated on cooling was filtered and discarded. The filtrate was successively washed with solutions of sodium bicarbonate, sodium thiosulfate and brine. After drying over sodium sulfate, the organic layer was concentrated to an oil which solidified on standing. Chromatographic purification afforded 0.29 g (17.2 percent) of the product sulfone, m.p. 150.5°–152° C.

Calculated for $C_{13}H_5Cl_2F_6N_3O_3S$: C, 33.35; H, 1.07; N, 8.97. Found: C, 32.68; H, 1.07; N, 8.81.

EXAMPLE 3

Preparation of 1-(2,6-dichloro-4-trifluoromethylphenyl)-3-cyano-4-trifluoromethylsulfinyl-5-methoxypyrazole Additionally, there was obtained from the reaction of EXAMPLE 2 a second product amounting to 0.63 g (38.7% yield) of the corresponding 1-(2,6-dichloro-4-trifluoromethylphenyl)-3-cyano-4-trifluoromethylsulfinyl-5-methoxypyrazole, m.p. 135.5°–137° C. An amount (0.8 g) of unreacted starting material was also recovered.

Calculated for $C_{13}H_5Cl_2F_6N_3O_2S$: C, 34.53; H, 1.11; N, 9.29. Found: C, 34.57; H, 1.11; N, 9.15.

EXAMPLE 4

Preparation of 1-(2,6-dichloro-4-trifluoromethylphenyl)-3-cyano-4-trifluoromethylsulfenyl-5-ethoxypyrazole a) Preparation of intermediate: 1-(2,6-Dichloro-4-trifluoromethylphenyl)-3-methoxycarbonyl-4-trifluoromethylsulfenyl-5-ethoxypyrazole The intermediate was prepared according to process SCHEME I of EXAMPLE 1c by reacting 1-(2,6-dichloro-4-trifluoromethylphenyl)-3-methoxycarbonyl-4-trifluoromethylsulfenyl-5-hydroxypyrazole with diethyl sulfate and sodium hydride in dioxane. The following spectral data were obtained: MS, m/e=482(M+); NMR (CDCl$_3$) δ1.43 (t, J=7.0 Hz, C$_2$H$_5$), 3.73 (s, OCH$_3$), 4.4 (q, J=7.0, OCH$_2$), and 7.76 (s, 2H aromatic).

b) Preparation of 1-(2,6-dichloro-4-trifluoromethylphenyl)-3-cyano-4-trifluoromethylsulfenyl-5-ethoxypyrazole Following synthetic process SCHEME I, in a similar manner to that of EXAMPLES 1d and 1e, there was obtained a solid, mp 108°–109° C.

EXAMPLE 5 a) Preparation of: 1-(2,6-dichloro-4-trifluoromethylphenyl)-3-cyano-4-dichlorofluoromethylsulfenyl-5-methoxypyrazole

Preparation of intermediate: 1-(2,6-dichloro-4-trifluoromethylphenyl)-3-methoxycarbonyl-4-dichlorofluoromethylsulfenyl-5-hydroxypyrazole The intermediate, prepared in a similar manner according to process SCHEME I of EXAMPLE 1b by reacting 1-(2,6-dichloro-4-trifluoromethylphenyl)-3-(methoxycarbonyl)-pyrazol-5-one with dichlorofluoromethanesulfenyl chloride in dichloromethane and pyridine, was obtained in 99% yield, m.p. 154°–156° C.

b) Preparation of intermediate: 1-(2,6-dichloro-4-trifluoromethylphenyl)-3-methoxycarbonyl-4-dichlorofluoromethylsulfenyl-5-methoxypyrazole To a solution of 4.14 g of 1-(2,6-dichloro-4-trifluoromethylphenyl)-3-methoxycarbonyl-4-dichlorofluoromethylsulfenyl-5-hydroxypyrazole in 180 ml of diethyl ether was added slowly a saturated solution of diazomethane in diethyl ether until all the starting material reacted (as monitored by t.l.c.). The reaction mixture was concentrated and the product was purified by chromatography to afford 3.5 g (82 percent yield) of a white solid, mp. 79°–80° C. NMR (CDCl$_3$): δ3.78 (s, OCH$_3$), 4.3 (s, CH$_3$) and 7.7 (s, 2H aromatic).

c) Preparation of 1-(2,6-dichloro-4-trifluoromethylphenyl)-3-cyano-4-dichlorofluoromethylsulfenyl-5-methoxypyrazole Following synthetic process SCHEME I, in a similar manner to that of EXAMPLES 1d and 1e, there was obtained a solid, mp 93.5°–95° C.

Similarly, using the procedures of EXAMPLES 1–5, there were obtained compounds of formula (III) wherein the substituent groups are as defined in TABLE 2.

TABLE 2

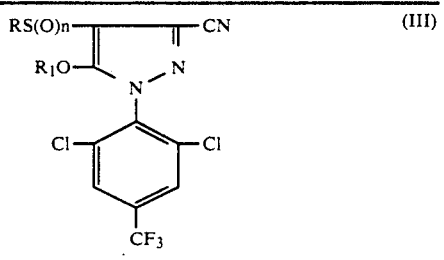

ADDITIONAL SYNTHESIZED PYRAZOLE COMPOUNDS OF FORMULA (III)

| EXAMPLE | Substituent R | n | R$_1$ | M.P. (°C.) |
|---|---|---|---|---|
| 6 | CF$_3$ | 1 | C$_2$H$_5$ | 156.5–157.5 |
| 7 | CF$_3$ | 2 | C$_2$H$_5$ | 131.5–133 |
| 8 | CClF$_2$ | 0 | C$_2$H$_5$ | 92–93.5 |
| 9 | CCl$_2$F | 1 | CH$_3$ | 136–138 |
| 10 | CCl$_2$F | 2 | CH$_3$ | 188.5–190 |
| 11 | CClF$_2$ | 1 | C$_2$H$_5$ | 161–162 |
| 12 | CClF$_2$ | 2 | C$_2$H$_5$ | 130–131 |
| 13 | CClF$_2$ | 0 | CH$_3$ | 87–88 |
| 14 | CClF$_2$ | 1 | CH$_3$ | 138.5–140 |
| 15 | CClF$_2$ | 2 | CH$_3$ | 166–167.5 |

EXAMPLE 16

MITICIDE, INSECTICIDE, AND NEMATICIDE USE

The following test procedures, using the compounds of EXAMPLES 1–15, were conducted in a greenhouse to determine the pesticidal use and activity of compounds of the invention against mites; certain insects, including an aphid, a caterpillar, a fly, and two species of beetle larvae (one foliar feeding and the other root feeding); and nematodes. The specific species tested were as follows:

| GENUS, SPECIES | COMMON NAME | (ABBREVIATION) |
|---|---|---|
| Tetranychus urticae | twospotted spider mite | TSM |
| Aphis nasturtii | buckthorn aphid | BA |
| Spodoptera eridania | southern armyworm | SAW |
| Epilachna varivestis | Mexican bean beetle (larva) | MBB |
| Musca domestica | housefly | HF |
| Diabrotica u. howardi | southern corn rootworm | SCRW |
| Meloidogyne incognita | southern root-knot nematode | SRKN |

Formulations

The test compounds (EXAMPLES 1–15) were formulated for use according to the following methods used for each of the test procedures.

For mites, aphids, southern armyworm, and Mexican bean beetle, a solution or suspension was prepared by adding 10 mg of the test compound to a solution of 160 mg of dimethylformamide, 838 mg of acetone, 2 mg of a 3:1 ratio of Triton X-172:Triton X-152 (respectively, mainly anionic and nonionic low foam emulsifiers which are each anhydrous blends of alkylaryl polyether alcohols with organic sulfonates), and 98.99 g of water. The result was a concentration of 100 ppm of the test compound.

For housefly, the formulation was initially prepared in a similar manner to the above, but in 16.3 g of water, providing a 200 ppm concentration. Final dilution with an equal volume of a 20% by weight aqueous solution of sucrose provided a 100 ppm concentration of the test compound. When necessary, sonication was provided to insure complete dispersion.

For southern corn rootworm, a solution or suspension was prepared in the same manner as that used for the initial 200 ppm concentration for housefly. Aliquots of this 200 ppm formulation were then used directly according to the required test concentration.

For southern root-knot nematode, a stock solution or suspension was prepared by adding 15 mg of the test compound to 250 mg of dimethylformamide, 1250 mg of acetone and 3 mg of the emulsifier blend referenced above. Water was then added to bring the total volume to 45 ml and a test compound concentration of 333 ppm. When necessary, sonication was provided to insure complete dispersion.

Test Procedures

The above formulated test compounds were then evaluated for their pesticidal activity at the specified concentrations, in ppm (parts per million) by weight, according to the following test procedures:

Twospotted spider mite:

Leaves infested with adult and nymphal stages of the twospotted spider mite, obtained from a stock culture were placed on the primary leaves of two bean plants growing in a 6 cm. peat pot. A sufficient number of mites (150–200) for testing were transferred to the fresh plants within a period of twenty-four hours. The potted plants (one pot per compound) were placed on a revolving turntable and sprayed, sufficient to wet the plants to runoff, with 100 ml of the 100 ppm test compound formulation by use of a DeVilbiss spray gun set at 40 psig. air pressure. As an untreated control, 100 ml of the water-acetone-DMF-emulsifier solution, containing no test compound, were also sprayed on infested plants. A treated control with a commercial technical compound, either dicofol or hexythiazox, formulated in the same manner, was periodically tested as a standard. The sprayed plants were held for six days, after which a mortality count of motile forms was made.

Buckthorn aphid:

Adult and nymphal stages of buckthorn aphid were reared on potted dwarf nasturtium plants. The potted plants (one pot per compound tested) infested with 100–150 aphids, were placed on a revolving turntable and sprayed with 100 ml of the 100 ppm test compound formulation by use of a DeVilbiss spray gun set at 40 psig air pressure. As an untreated control, 100 ml of a water-acetone-DMF-emulsifier solution, containing no test compound, were also sprayed on infested plants. A treated control with a commercial technical compound, malathion, formulated in the same manner, was periodically tested as a standard. After spraying, the pots were stored for one day after which the dead aphids were counted.

Southern armyworm:

Potted bean plants, infested with second instar larvae of Southern armyworm, were placed on a revolving turntable and sprayed with 100 ml of the 100 ppm test compound formulation by use of a DeVilbiss spray gun set at 40 psig air pressure. As an untreated control, 100 ml of a water-acetone-DMF-emulsifier solution, containing no test compound, were also sprayed on plants. A treated control with a commercial technical compound, either cypermethrin or sulprofos, formulated in the same manner, was periodically tested as a standard. When dry, the leaves were placed in a plastic cup lined with moistened filter paper. Five randomly selected larvae were introduced into each dish which was closed and held for five days. Although the larvae could easily consume the whole leaf within twenty-four hours, no more food was added. Larvae which were unable to move the length of the body, even upon stimulation by prodding, were considered dead.

Mexican bean beetle:

Potted bean plants, infested with second instar larvae of Mexican bean beetle, were placed on a revolving turntable and sprayed, sufficient to wet the plants to runoff, by use of a DeVilbiss spray gun set at 40 psig air pressure. As an untreated control, 100 ml of a water-acetone-DMF-emulsifier solution, containing no test compound, were also sprayed on plants. A treated control with a commercial technical compound, either cypermethrin or sulprofos, formulated in the same manner, was periodically tested as a standard. When dry, the leaves were placed in a plastic cup lined with moistened filter paper. Five randomly selected larvae were introduced into each dish which was closed and held for five days. Although the larvae could easily consume the leaf within 24 to 48 hours, no more food was added. Larvae which were unable to move the length of the body, even upon stimulation by prodding, were considered dead.

House fly:

Four to six day old adult house flies were reared according to the specifications of the Chemical Specialties Manufacturing Association (Blue Book, McNair-Dorland Co., N.Y. 1954; pages 243-244, 261) under controlled conditions. The flies were immobilized by anesthetizing with carbon dioxide and twenty five immobilized individuals, males and females, were transferred to a cage consisting of a standard food strainer and a wrapping-paper-covered surface. Ten ml of the 100 ppm test compound formulation were added to a soufflé cup containing an absorbent cotton pad. As an untreated control, 10 ml of a water-acetone-DMF-emulsifier-sucrose solution, containing no test compound, were applied in a similar manner. A treated control with a commercial technical compound, malathion, formulated in the same manner, was periodically tested as a standard. The bait cup was introduced inside the food strainer prior to admitting the anesthetized flies. After 24 hours, flies which showed no sign of movement on prodding were considered dead.

Southern corn rootworm:

Into a jar containing 60 g of sandy loam soil was added an aliquot of the 200 ppm test compound formulation (as appropriate for the final soil concentration of the test compound), 3.2 ml of water and five pregerminated corn seedlings. The jar was shaken thoroughly to obtain an even distribution of the test formulation. Following this, twenty southern corn rootworm eggs were placed into a cavity, which was made in the soil. Vermiculite(1 ml) and water (1.7 ml) were then added to this cavity. In a similar manner, an untreated control was prepared by application of the same size aliquot of a water-acetone-DMF-emulsifer solution, containing no test compound. Additionally, a treated control with a commercial technical compound (selected typically from terbufos, fonofos, phorate, chlorpyrifos, carbofuran, isazophos, or ethoprop), formulated in the same manner was periodically used as a test standard. After 7 days, the living rootworm larvae were counted using a well known "Berlese" funnel extraction method.

Southern root-knot nematode:

Infected roots of tomato plants, containing egg masses of southern root-knot nematode, were removed from a stock culture and cleaned of soil by shaking and washing with tap water. The nematode eggs were separated from the root tissue and rinsed with water. Samples of the egg suspension were placed on a fine screen over a receiving bowl, in which the water level was adjusted to be in contact with the screen. From the bowl, juveniles were collected on a fine screen. The bottom of a cone-shaped container was plugged with coarse vermiculite and then filled to within 1.5 cm of the top with about a 200 ml volume of pasturized soil. Then into a hole made in the center of the soil in the cone was pipetted an aliquot of the 333 ppm test compound formulation. A treated control with a commercial technical compound, fenamifos, formulated in a similar manner, was periodically tested as a standard. As an untreated control, an aliquot of a water-acetone-DMF-emulsifier solution, containing no test compound, was applied in a similar manner. Immediately after treatment of the soil with the test compound there were added to the top of each cone 1000 second stage juvenile southern root-knot nematodes. After 3 days, a single healthy tomato seedling was then transplanted into the cone. The cone, containing the infested soil and tomato seedling, was kept in the greenhouse for 3 weeks. At the termination of the test, roots of the tomato seedling were removed from the cone and evaluated for galling on a rating scale relative to the untreated control as follows:

1—severe galling, equal to untreated control
3—light galling
4—very light galling
5—no galling, i.e., complete control These results were then converted to an $ED_3$ or $ED_5$ value (effective dose to provide a 3 or 5 gall rating).

Use Results

Results of miticidal, insecticidal, and nematicidal activity for compound EXAMPLES 1-15 of the invention are discussed below and set forth in TABLE 3 against the indicated test species (BA, SAW, MBB, HF, and SCRW: designated by common name abbreviations) and at the indicated dosage rates. Results are presented in percent mortality. The compounds of the invention also provide some control of mites (where the compound of EXAMPLE No. 6 gave about 30-70% mortality of TSM at 100 ppm as a foliar application) and soil nematodes (where compounds of EXAMPLE Nos. 2 and 9 provided ED$_3$ values of 11 and 21-42, respectively, for SRKN). Furthermore, compounds of the invention exhibit reduced or antifeeding properties for some pest species, for example for foliar pests such as southern armyworm and Mexican bean beetle.

The compounds of the invention have utility against various pest species at even lower rates, for example: for foliar application, rates in the range of about 50-0.5 ppm, or less, may be useful; for bait application, rates in the range of about 50-0.05 ppm, or less, may be useful; and for soil application, rates in the range of about 1.0-0.01 ppm, or less, may be useful.

TABLE 3
USE EXAMPLE OF PESTICIDAL
ACTIVITY OF PYRAZOLE COMPOUNDS

| EX-AMPLE | Percent Mortality | | | | |
|---|---|---|---|---|---|
| | Foliar or Bait Application at 100 ppm | | | | Soil conc. - 1.45 ppm |
| | BA | SAW | MBB | HF | SCRW |
| 1 | 100 | 50 | 0-30 | 70-100 | 100 |
| 2 | 100 | 100 | 70-100 | 70-100 | 100 |
| 3 | 100 | 100 | 70-100 | 70-100 | 100 |
| 4 | 100 | 90 | 0-30 | 70-100 | 100 |
| 5 | 100 | 100 | 70-100 | 70-100 | 100 |
| 6 | 100 | 100 | 70-100 | 70-100 | 100 |
| 7 | 100 | 100 | 30-70 | 70-100 | 100 |
| 8 | 70 | 100 | 30-70 | 70-100 | 100 |
| 9 | 100 | 100 | 70-100 | 70-100 | 100 |
| 10 | 0 | 100 | 0-30 | 70-100 | 100 |
| 11 | 80 | 100 | 0-30 | 70-100 | 100 |
| 12 | 100 | 100 | 70-100 | 70-100 | 100 |
| 13 | 100 | 100 | 0-30 | 70-100 | 100 |
| 14 | 0 | 100 | 0-30 | 70-100 | 100 |
| 15 | 100 | 100 | 70-100 | 70-100 | 100 |

METHODS AND COMPOSITIONS

As is evident from the foregoing pesticidal uses, the compounds of the present invention provide activity and methods of control against a number of species which includes arthropods, especially insects, plant nematodes, and helminth and protozoan pests. The compounds thus are advantageously employed in practical uses, for example, in agricultural and horticultural crops, forestry, veterinary medicine and livestock husbandry, and in public health.

A feature of the present invention therefore provides a method of control of pests at a locus which comprises the treatment of the locus (e.g., by application or administration) with an effective amount of a compound of general formula (I) and more preferably a compound of formula (II) or (III), wherein the substituent groups are as hereinbefore defined. The locus includes, for example, the pest itself or the place (plant, animal, person, field, structure, premises, forest, orchard, waterway, soil, plant or animal product, and the like) where the pest resides or feeds.

The compounds of this invention are preferably used to control soil insects, such as corn rootworm, termites (especially for protection of structures), root maggots, wireworms, root weevils, stalkborers, cutworms, root aphids, and grubs. They may also be used to provide activity against plant pathogenic nematodes, such as root-knot, cyst, dagger, lesion, and stem and bulb nematodes, and against mites. For the control of soil pests, for example corn rootworm, the compounds are advantageously applied to or incorporated at an effective rate into the soil in which crops are planted or to be planted or to the seeds or growing plant roots.

Furthermore, these compounds may be useful in the control via foliar application or systemic action of some arthropods, especially some insects, which feed on the above ground portions of plants.

In the area of public health, the compounds are especially useful in the control of many insects, especially filth flies and other Dipteran pests, such as houseflies, stableflies, soldierflies, hornflies, deerflies, horseflies, midges, punkies, blackflies, and mosquitoes.

Compounds of the invention may be used in the following applications and on the following pests including arthropods, especially insects, nematodes, and helminth and protozoan pests:

In the protection of stored products, for example cereals, including grain and flour, groundnuts, animal feedstuffs, timber and household goods, e.g. carpets and textiles, compounds of the invention are useful against attack by arthropods, more especially beetles, including weevils, moths and mites, for example Ephestia spp. (flour moths), Anthrenus spp. (carpet beetles), Tribolium spp. (flour beetles), Sitophilus spp. (grain weevils) and Acarus spp. (mites).

In the control of cockroaches, ants and termites and similar arthropod pests in infested domestic and industrial premises and in the control of mosquito larvae in waterways, wells, reservoirs or other running or standing water.

For the treatment of foundations, structures and soil in the prevention of the attack on building by termites, for example, Reticulitermes spp., Heterotermes spp., Coptotermes spp.

In agriculture against adults, larvae and eggs of Lepidoptera (butterflies and moths), e.g. Heliothis spp. such as *Heliothis virescens* (tobacco budworm), *Heliothis armigera* and *Heliothis zea*, Spodoptera spp. such as *S. exempta*, *S. littoralis* (Egyptian cotton worm), *S. eridania* (southern army worm), and *Mamestra configurata* (bertha army worm); Earias spp. e.g. *E. insulana* (Egyptian bollworm), Pectinophora spp. e.g. *Pectinophora gossypiella* (pink bollworm), Ostrinia spp. such as *O. nubilalis* (European cornborer), *Trichoplusia ni* (cabbage looper), Pieris spp. (cabbage worms), Laphygma spp. (army worms), Agrotis and Amathes spp. (cutworms), Wiseana spp. (porina moth), Chilo spp. (rice stem borer), Tryporyza spp. and Diatraea spp. (sugar cane borers and rice borers), *Sparganothis pilleriana* (grape berry moth), *Cydia pomonella* (codling moth), Archips spp. (fruit tree tortrix moth), *Plutella xylostella* (diamond back moth), *Bupalus piniarius*, *Cheimatobia brumata*, *Lithocolletis blancardella*, *Hyponomeuta padella*, *Plutella maculipennis*, *Malacosoma neustria*, *Euproctis chrysorrhoea*, Lymantria spp. *Bucculatrix thurberiella*, *Phyllocnistis citrella*, Euxoa spp., *Feltia brassicae*, *Panolis flammea*, *Prodenia litura*, *Carpocapsa pomonella*, *Pyrausta nubilelis*, *Ephestia kuehniella*, *Galleria mellonella*, *Tineola bisselliella*, *Tinea pellionella*, *Hofmannophila pseudospretella*, *Cacoecia podana*, *Capus reticulana*, *Choristoneura fumiferana*, *Clysia ambiguells*, *Homona magnanime* and *Tortix viridana*.

Against adult and larvae of Coleoptera (beetles) e.g. *Hypothenemus hampei* (coffee berry borer), Hylesinus spp. (bark beetles), *Anthonomus grandis* (cotton boll weevil), Acalymma spp. (cucumber beetles), Lema spp., Psylliodes spp., *Leptinotarsa decemlineata* (Colorado potato beetle), Diabrotica spp. (corn rootworms), Gonocephalum spp. (false wire worms), Agriotes spp. Limonius spp. (wireworms), Dermolepida, Popillia spp. Heteronychus spp. (white grubs), *Phaedon cochleariae*

(mustard beetle), *Lissorhoptrus oryzophilus* (rice water weevil), Meligethes spp. (pollen beetles), Ceutorhynchus spp., Rhynchophorus and Cosmopolites spp. (root weevils), *Anobium punctatum, Rhizopertha dominica, Bruchidius obtectus, Acanthoscelides obtectus, Hylotrupes bajulus, Agelastica alni, Phaedon cochleariae, Psylliodes chrysocephala, Epilachna varivestis*, Atomaria spp., *Oryzaephilus surinamensis*, Anthonomus spp., Sitophilus spp., *Otiorrhynchus sulcatus, Cosmoplites sordidus, Ceuthorrhynchus assimilis, Hypera postics*, Dermestes spp., Trogoderma spp., Anthrenus spp., Attagenus spp., Lyctus spp., *Maligethes aeneus*, Ptinus spp., *Niptus hololeucrys. Gibbium psylloides*, Tribolium spp., *Tenebrio molitor*, Agriotes spp., Conoderus spp., *Melolontha melolontha, Amphimallon solstitialis* and *Costelytra zealandica*.

Against Heteroptera (Hemiptera and Homoptera) e.g. Psylla spp., Bemisia spp., Trialeurodes spp., Aphis spp., Myzus spp., *Megoura viciae*, Phylloxera spp., Adelges spp., *Phorodon humuli* (hop damson aphid), Aeneolamia spp., Nephotettix spp. (rice leaf hoppers), Empoasca spp., Nilaparvata spp., Perkinsiella spp., Pyrilla spp., Aonidiella spp. (red scales), Coccus spp., Pseucoccus spp., Helopeltis spp. (mosquito bugs), Lygus spp., Dysdercus spp., Oxycarenus spp., Nezara spp., Eurygaster spp., *Piesma quadrata, Cimex lectularius, Rhodnius prolixus* and Triatoma spp. *Aspidiotus hederae, Aeurodes brassicae, Brevicoryne brassicae, Cryptomyzus ribis, Doralis fabae, Doralis pomi., Eriosoma lanigerum, Hyalopterus arundinis, Macrosiphum avenae*, Myzus spp., *Phorodon humuli, Rhopalosiphum padi, Euscelis bilobatus, Nephotettix cincticeps, Lecanium corni, Saissetia oleae, Laodelphax striatellus*.

Against Hymenoptera e.g. Athalia spp. and Cephus spp. (saw flies), Atta spp. (leaf cutting ants), Diprion spp., Hopolocampa spp., Lasius spp., Monomorium spp., Vespa spp., and Solenopsis spp.

Against Diptera e.g. Delia spp. (root maggots), Atherigona spp. and Chlorops spp; Sarcophaga spp; Musca spp, Phormia spp, Aedes spp, Anopheles spp, Simulium spp, (shoot flies), Phytomyza spp. (leaf miners), Ceratitis spp. (fruit flies), Culex spp., *Drosophila melanogaster, Ceratitis capitata, Dacus oleae, Tipula paludosa, Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Fannia spp., *Bibio hortulanus, Oscinella frit*, Phorbia spp., *Pegomyia hyoscyani*.

Against Thysanoptera such as *Thrips tabaci* and *Hercinothrips femoralis*.

Against Orthoptera such as Locusta and Schistocerca spp., (locusts and crickets) e.g. Gryllus spp., and Acheta spp. for example, *Blatta orientalis, Periplaneta americana, Leucophaea maderae, Blatella germanica, Acheta domesticus*, Gryllotalpa spp., *Locusta migratoria migratorioides, Melanoplus differentialis* and *Schistocerca gregaria*.

Against Collembola e.g. Sminthurus spp. and Onychiurus spp. (springtails); Periplaneta spp. and Blattela spp. (roaches).

Against Isoptera e.g. Odontotermes spp., Reticuletermes spp., Coptotermes spp. (termites).

Against Dermaptera e.g. Forticula sp. (earwigs).

Against arthropods of agricultural significance such as Acari (mites) e.g. Tetranychus spp.; Panonychus spp. and Bryobia spp. (spider mites), Eriophyes spp. (gall mites).

Against Thysanura, for example *Lepisma saccharian*.

Against Anoplura for example, *Phylloxera vastatrix*, Pemphigus spp., *Pediculus humanus corporis*, Haematopinus spp. and Linognathus spp.

Against Mallophaga, for example, Trichodectes spp. and Damalinea spp.

Against Siphonoptera, for example, *Xenopsylla cheopis* and Ceratophyllus spp.

Against other arthropods, such as Polyphadotarsonemus spp.; Blaniulus spp. (millipedes), Scutigerella spp. (symphilids), Oniscus spp. (woodlice) and Triops spp. (crustacea).

Against Isopoda, for example, *Oniseus asellus, Armadillidium vulgare* and *Porcellio scaber*.

Against Chilopoda, for example, *Geophilus carpophagus* and *Scutigera spex*.

Against nematodes which attack plants and trees of importance to agriculture, forestry and horticulture either directly or by spreading bacterial, viral, mycoplasma or fungal diseases of the plants. For example root-knot nematodes such as Meloidogyne spp. (e.g. *M. incognita*); cyst nematodes such as Globodera spp. (e.g. *G. rostochiensis*); Heterodera spp. (e.g. *H. avenae*); Radopholus spp. (e.g. *R. similis*; lesion nematodes such as Pratylenchus spp. (e.g. *P. pratensis*); Belonolaimus spp. (e.g. *B. gracilis*); Tylenchulus spp. (e.g. *T. semipenetrans*); Rotylenchulus spp. (e,g. *R. reniformis*); (e.g. *H. multicinctus*); Hemicycliophora spp. (e.g. *H. gracilis*); Criconemoides spp. (e.g. *C. similis*); Trichodorus spp. (e.g. *T. primitivus*); dagger nematodes such as Xiphinema spp. (e.g. *X. diversicaudatum*), Longidorus spp. (e.g. *L. elongatus*); Hoplolaimus spp. (e.g. *H. coronatus*); Aphelenchoides spp. (e.g. *A. ritzema-bosi, A. besseyi*); stem and bulb eelworm such as Ditylenchus spp. (e.g. *D. dipsaci*).

In the field of veterinary medicine and livestock husbandry and in the maintenance of public health against arthropods, helminths or protozoa which are parasitic internally or externally upon vertebrates, particularly warm-blooded vertebrates, for example man and domestic animals, e.g. cattle, sheep, goats, equines, swine, poultry, dogs, cats and fishes, for example Acarina, including ticks (e.g. Ixodes spp., Boophilus spp. e.g. *Boophilus microplus*, Amblyomma spp., Hyalomma spp., Rhipicephalus spp. e.g. *Rhipicephalus appendiculatus*, Haemaphysalis spp., Dermacentor spp., Ornithodorus spp. (e.g. *Ornithodorus moubata*) and mites (e.g. Damalinia spp., *Dermahyssus gallinae*, Sarcoptes spp. e.g. *Sarcoptes scabiei*, Psoroptes spp., Chorioptes spp., Demodex spp., Eutrombicula spp.,); Diptera (e.g. Aedes spp., Anopheles spp., Musca spp., Hypoderma spp., Gasterophilus spp., Simulium spp); Hemiptera (e.g. Triatoma spp); Phthirapter (e.g. Damalinia spp., Linognathus spp.); Siphonaptera (e.g. Ctenocephalides spp.); Dictyoptera (e.g. Periplaneta spp., Blatella spp.); Hymenoptera (e.g. Monomorium pharaonis); for example against infections of the gastro-intestinal tract caused by parasitic nematode worms, for example members of the family Trichostrongylidae, *Nippostrongylus brasiliensis, Trichinella spiralis, Haemonchus contortus, Trichostrongylus colubriformis, Nematodirus batus, Ostertagis circumcincta, Trichostrongylus axei*, Cooperia spp. and *Hymenolepis nana*; in the control and treatment of protozoal diseases caused by, for example, Eimeria spp. e.g. *Eimeria tenella, Eimeria acervulina, Eimeria brunetti, Eimeria maxima* and *Eimeria necatrix, Trypanosoms cruzi*, Leishaminia spp., Plasmodium spp., Babesis spp., Trichomonadidae spp., Histomanas spp., Giardia spp., Toxoplasma spp., *Entamoeba histolytica* and Theileria spp.

The invention, as previously described, provides methods of control of pests via application or administration of an effective amount of compounds of formula (I) or (II) or (III) at a locus which comprises treatment of the locus.

In practical use for the control of arthropod, especially insect, and nematode pests of plants, a method, for example, comprises application to the plants or to the medium in which they grow an effective amount of a compound of the invention. For such a method, the active compound is generally applied to the locus in which the arthropod or nematode infestation is to be controlled at an effective rate in the range of about 0.005 kg to about 15 kg of the active compound per hectare of locus treated. Under ideal conditions, depending on the pest to be controlled, a lower rate may offer adequate protection. On the other hand, adverse weather conditions, resistance of the pest and other factors may require that the active ingredient be used at higher rates. The optimum rate depends usually upon a number of factors, for example, the type of pest being controlled, the type and the growth stage of the infested plant, the row spacing and also the method of application. More preferably an effective rate range of the active compound is from about 0.01 kg/ha to about 2 kg/ha.

When a pest is soil-borne, the active compound generally in a formulated composition, is distributed evenly over the area to be treated (i.e., for example broadcast or band treatment) in any convenient manner. Application may be made, if desired, to the field or cropgrowing area generally or in close proximity to the seed or plant to be protected from attack. The active component can be washed into the soil by spraying with water over the area or can be left to the natural action of rainfall. During or after application, the formulated compound can, if desired, be distributed mechanically in the soil, for example by ploughing, disking, or use of drag chains. Application can be prior to planting, at planting, after planting but before sprouting has taken place, or after sprouting. Additionally, a method of control may also comprise treatment of the seed prior to planting with subsequent control effected after planting the seed.

Methods of control of pests also consist of application to or treatment of the foliage of plants to control arthropods, especially insects, and nematodes attacking the aerial parts of the plants. In addition, methods of control of pests by the invention compounds are provided to control pests which feed on parts of the plant remote from the point of application, e.g., leaf feeding insects which are controlled via systemic action of the active compound when applied for example to the roots of a plant. Furthermore, the compounds of the invention may reduce attacks on a plant by means of antifeeding or repellent effects.

The compounds of the invention and methods of control of pests therewith are of particular value in the protection of field, forage, plantation, glasshouse, orchard and vineyard crops, of ornamentals, and of plantation and forest trees, for example: cereals (such as maize, wheat, rice, and sorghum), cotton, tobacco, vegetables (such as beans, cole crops, curcurbits, lettuce, onions, tomatoes and peppers), field crops (such as potatoes, sugar beets, ground nuts, soybeans, and oil seed rape), sugar cane, grassland and forage crops (such as maize, sorghum, and lucerne), plantations (such as tea, coffee, cocoa, banana, palm oil, coconut, rubber, and spices), orchards and groves (such as of stone and pit fruit, citrus, kiwifruit, avocado, mango, olives and walnuts), vineyards, ornamental plants, flowers and vegetables and shrubs under glass and in gardens and parks, and forest trees (both deciduous and evergreen) in forests, plantations and nurseries.

They are also valuable in the protection of timber (standing, felled, converted, stored or structural) from attack, for example, by sawflies or beetles or termites.

They have applications in the protection of stored products such as grains, fruits, nuts, spices and tobacco, whether whole, milled or compounded into products, from moth, beetle, mite and grain weevil attack. Also protected are stored animal products such as skins, hair, wool and feathers in natural or converted form (e.g. as carpets or textiles) from moth and beetle attack as well as stored meat and fish from beetle, mite and fly attack.

Additionally, the compounds of the invention and methods of use thereof are of particular value in the control of arthropods, helminths or protozoa which are injurious to, or spread or act as vectors of diseases in man and domestic animals, for example those hereinbefore mentioned, and more especialy in the control of ticks, mites, lice, fleas, midges and biting, nuisance and myiasis flies. The compounds of the invention are particularly useful in controlling arthropods, helminths or protozoa which are present inside domestic host animals or which feed in or on the skin or suck the blood of the animal, for which purpose they may be administered orally, parenterally, percutaneously or topically.

Furthermore, compounds of the invention may be useful for coccidiosis, a disease caused by infections from protozoan parasites of the genus *Eimeria*. It is an important potential cause of economic loss in domestic animals and birds, particularly those raised or kept under intensive conditions. For example, cattle, sheep, pigs and rabbits may be affected, but the disease is especially important in poultry, particularly in chickens. Administration of a small amount of a compound of the invention, preferably by a combination with feed is effective in preventing or greatly reducing the incidence of coccidiosis. The compounds are effective against both the cecal form and the intestinal forms. Furthermore, the compounds of the invention may also exert an inhibiting effect on oocysts by greatly reducing the number and sporulation of those produced. The poultry disease is generally spread by the birds picking up the infectious organism in dropings in or on contaminated litter, ground, food, and drinking water. The disease is manifested by hemorrhage, accumulation of blood in the ceca, passage of blood to the droppings, weakness and digestive disturbances. The disease often terminates in the death of the animal, but the fowl which survive severe infections have had their market value substantially reduced as a result of the infection.

The compositions hereinafter described for application to growing crops and crop growing loci and as a seed dressing may, in general, alternatively be employed for topical application to man and animals and in the protection of stored products, household goods, property and areas of the general environment. Suitable means of applying the compounds of the invention include:

to growing crops as foliar sprays, dusts, granules, fogs and foams and also as suspensions of finely divided and encapsulated compositions as soil and root treatments by liquid drenches, dusts, granules, smokes and foams; to seeds of crops via application as seed dressings by liquid slurries and dusts;

to persons or animals infested by or exposed to infestation by arthropods, helminths or protozoa, by parenteral, oral or topical application of compositions in which the active ingredient exhibits an immediate and/or prolonged action over a period of time against the arthropods, helminths or protozoa, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax smears and livestock self-treatment systems;

to the environment in general or to specific locations where pests may lurk, including stored products, timber, household goods, and domestic and industrial premises, as sprays, fogs, dusts, smokes, wax-smears, lacquers, granules and baits, and in tricklefeeds to waterways, wells, reservoirs and other running or standing water;

to domestic animals in feed to control fly larvae feeding in their feces;

In practice, the compounds of the invention most frequently form parts of compositions. These compositions can be employed to control arthopods, especially insects, nematodes, and helminth and protozoan pests. The compositions may be of any type known in the art suitable for application to the desired pest in any premises or indoor or outdoor area or by internal or external administration to vertebrates. These compositions contain at least one compound of the invention, such as described earlier, as the active ingredient in combination or association with one or more other compatible components which are for example, solid or liquid carriers or diluents, adjuvants, suface-active-agents, and the like appropriate for the intended use and which are agronomically or medicinally acceptable. These compositions, which may be prepared by any manner known in the art, likewise form a part of this invention.

These compositions may also contain other kinds of ingredients such as protective colloids, adhesives, thickeners, thixotropic agents, penetrating agents, spray oils (especially for acaridical use), stabilizers, preservative agents (especially mold preservatives), sequestering agents, or the like, as well as other known active ingredients with pesticidal properties (particularly insecticidal, miticidal, nematicidal, or fungicidal) or with properties regulating the growth of plants. More generally, the compounds employed in the invention may be combined with all the solid or liquid additives corresponding to the usual techniques of formulation.

Compositions, suitable for applications in agriculture, horticulture, and the like include formulations suitable for use as, for example, sprays, dusts, granules, fogs, foams, emulsions and the like.

Compositions suitable for administration to vertebrates or man, include preparations suitable for oral, parenteral, percutaneous, e.g. pour-on, or topical administration.

Compositions for oral administration comprise one or more of the compounds of general formula(I) in association with pharmaceutically acceptable carriers or coatings and include, for example, tablets, pills, capsules, pastes, gels, drenches, medicated feeds, medicated drinking water, medicated dietary supplements, slow-release boluses or other slow-release devices intended to be retained within the gastrointestinal tract. Any of these may incorporate the active ingredient contained within microcapsules or coated with acid-labile or alkalilabile or other pharmaceutically acceptable enteric coatings. Feed premixes and concentrates containing compounds of the present invention for use in preparation of medicated diets, drinking water or other materials for consumption by animals may also be used.

Compositions for parenteral administration include solutions, emulsions or suspensions in any suitable pharmaceutically acceptable vehicle and solid or semisolid subcutaneous implants or pellets designed to release the active ingredient over a protracted period of time and may be prepared and made sterile in any appropriate manner known to the art.

Compositions for percutaneous and topical administration include sprays, dusts, baths, dips, showers, jets, greases, shampoos, creams, wax-smears, or pour-on preparations and devices (e.g. ear tags attached externally to animals in such a way as to provide local or systemic arthropod control).

Solid or liquid baits, suitable for controlling arthropods, comprise one or more compounds of general formula(I) and a carrier or diluent which may include a food substance or some other substance to induce consumption by the arthropod.

The effective use doses of the compounds employed in the invention can vary within wide limits, particularly depending on the nature of the pest to be eliminated and degree of infestation, for example, of crops with these pests. In general, the compositions according to the invention usually contain about 0.05 to about 95% (by weight) of one or more active ingredients according to the invention, about 1 to about 95% of one or more solid or liquid carriers and, optionally, about 0.1 to about 50% of one or more other compatible components, such as surface-active agents and the like.

In the present account, the term "carrier" denotes an organic or inorganic ingredient, natural or synthetic, with which the active ingredient is combined to facilitate its application, for example, to the plant, to seeds or to the soil. This carrier is therefore generally inert and it must be acceptable (for example, agronomically acceptable, particularly to the treated plant).

The carrier may be a solid, for example, clays, natural or synthetic silicates, silica, resins, waxes, solid fertilizers (for example ammonium salts), ground natural minerals, such as kaolins, clays, talc, chalk, quartz, attapulgite, montmorillonite, bentonite or diatomaceous earth, and ground synthetic minerals, such as silica, alumina, and silicates especially aluminium or magnesium silicates. As solid carriers for granules the following are suitable: crushed and fractionated natural rocks such as calcite, marble, pumice, sepiolite and dolomite; synthetic granules of inorganic and organic meals; granules of organic material such as sawdust, coconut shells, corn cobs, corn husks and tobacco stalks; and kieselguhr, tricalcium phosphate, powdered cork, absorbent carbon black, and water soluble polymers, resins, waxes, and solid fertilizers. Such solid compositions may, if desired, contain one or more compatible wetting, dispersing, emulsifying or colouring agents which, when solid, may also serve as a diluent.

The carrier may also be liquid, for example: water; alcohols, particularly butanol or glycol, as well as their ethers or esters, particularly methylglycol acetate; ketones, particularly acetone, cyclohexanone, methylethyl ketone, methylisobutylketone, and isophorone; petroleum fractions such as paraffinic or aromatic hydrocarbons, particularly xylenes or alkyl naphthalenes, and mineral and vegetable oils; aliphatic chlorinated hydrocarbons, particularly trichloroethane or methylene chloride, or aromatic chlorinated hydrocarbons, particularly chlorobenzenes; water-soluble or strongly polar solvents such as dimethylformamide, dimethyl sulphoxide, or N-methylpyrrolidone; liquefied gases; and the like or a mixture thereof.

The surface-active agent may be an emulsifying agent, dispersing agent or wetting agent of the ionic or non-ionic type or a mixture of such surface-active agents. Amongst these are e.g., salts of polyacrylic acids, salts of lignosulphonic acids, salts of phenolsulphonic or naphthalenesulphonic acids, polycondensates of ethylene oxide with fatty alcohols or fatty acids or fatty esters or fatty amines, substituted phenols (particularly alkylphenols or arylphenols), salts of sulphosuccinic acid esters, taurine derivatives (particularly alkyltaurates), phosphoric esters of alcohols or of polycondensates of ethylene oxide with phenols, esters of fatty acids with polyols, and sulphate, sulphonate and phosphate functional derivatives of the above compounds. The presence of at least one surface-active agent is generally essential when the active ingredient and/or the inert carrier are only slightly water soluble or are not water soluble and the carrier agent of the composition for application is water.

Compositions of the invention may further contain different other additives such adhesives and colorants. Adhesives such as carboxymethylcellulose and natural and synthetic polymers in the form of powders, granules or lattices, such as arabic gum, polyvinyl alcohol and polyvinyl acetate, natural phospholipids, such as cephalins and lecithins, and synthetic phospholipids can be used in the formulations. It is possible to use colorants such as inorganic pigments, for example: iron oxides, titanium oxides and Prussian Blue; organic dyestuffs, such as alizarin dyestuffs, azo dyestuffs and metal phthalocyanine dyestuffs; and trace nutrients such as salts of iron, manganese, boron, copper, cobalt, molybdenum and zinc.

Compositions containing compounds of general formula(I) which may be applied to control arthropod, plant nematode, helminth or protozoan pests, may also contain synergists (e.g. piperonyl butoxide or sesamex), stabilizing substances, other insecticides, acaricides, plant nematocides, anthelmintics or anticoccidials, fungicides (agricultural or veterinary as appropriate, e.g. benomyl and iprodione), bactericides, arthropod or vertebrate attractants or repellents or pheromones, deodorants, flavouring agents, dyes, and auxiliary therapeutic agents, e.g. trace elements. These may be designed to improve potency, persistence, safety, uptake where desired, spectrum of pests controlled or to enable the composition to perform other useful functions in the same animal or area treated.

Examples of other pesticidally-active compounds which may be included in, or used in conjunction with the compositions of the present invention are: acephate, chlorpyrifos, demeton-S-methyl, disulfoton, ethoprofos, fenitrothion, malathion, monocrotophos, parathion, phosalone, pirimiphos-methyl, triazophos, cyfluthrin, cyermethrin, deltamethrin, fenpropathrin, fenvalerate, permethrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectins, milbemycins, thiophanate, trichlorfon, dichlorovos, diaveridine and dimetriadazole.

For their agricultural application, the compounds of the formula(I) are therefore generally in the form of compositions, which are in various solid or liquid forms.

Solid forms of compositions which can be used are dusting powders (with a content of the compound of formula(I) ranging up to 80%), wettable powders and granules (including water dispersible granules), particularly those obtained by extrusion, compacting, impregnation of a granular carrier, or granulation starting from a powder (the content of the compound of formula(I) in these wettable powders or granules being between about 0.5 and about 80%). Solid homogenous or heterogenous compositions containing one or more compounds of general formula(I) for example granules, pellets, briquettes or capsules, may be used to treat standing or running water over a period of time. A similar effect may be achieved using trickle or intermittent feeds of water dispersible concentrates as described herein.

Liquid compositions, for example, include aqueous and nonaqueous solutions and suspensions (such as emulsifiable concentrates, emulsions, flowables, dispersions, and solutions) and aerosols. Liquid compositions also include, in particular, emulsifiable concentrates, dispersions, emulsions, flowables, aerosols, wettable powders (or powder for spraying), dry flowables and pastes as forms of compositions which are liquid or intended to form liquid compositions when applied, for example as aqueous sprays (including low and ultralow volume) and as fogs and aerosols.

Liquid compositions, for example, in the form of emulsifiable or soluble concentrates most frequently comprise about 5 to about 80% by weight of the active ingredient, while the emulsions or solutions which are ready for application contain, in their case, about 0.01 to about 20% of the active ingredient. Besides the solvent, the emulsifiable or soluble concentrates may contain, when required, about 2 to about 50% of suitable additives, such as stabilizers, surface-active agents, penetrating agents, corrosion inhibitors, colorants or adhesives. Emulsions of any required concentration, which are particularly suitable for application, for example, to plants, may be obtained from these concentrates by dilution with water. These compositions are included within the scope of the compositions which may be employed in the present invention. The emulsions may be in the form of water-in-oil or oil-in-water type and they may have a thick consistency.

The liquid compositions of this invention may, in addition to normal agricultural use applications be used for example to treat substrates or sites infested or liable to infestation by arthropods (and other pests controlled by compounds of this invention) including premises, outdoor or indoor storage or processing areas, containers or equipment and standing or running water.

All these aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (e.g. low or ultra-low volume) depending upon the need and application technique. The products and compositions according to the invention are conveniently applied to vegetation and in particular to roots or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil and for systemic pesticides.

The concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble. Some organic solids or inorganic salts may be dissolved in the carrier to help prevent settling or as antifreezes for water.

The wettable powers (or powder for spraying) are usually prepared so that they contain from about 10 to about 80% by weight of active ingredient, from about 20 to about 90% of a solid carrier, from about 0 to about 5% of a wetting agent. from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient(s) is(are) thoroughly mixed in a suitable blender with additional substances which may be impregnated on the porous filler and is(are) ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have a composition which is substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of dispersing agent or binder, followed by drying and screening), or by a dry route (compacting followed by grinding and screening).

The application dose (effective dose) of active ingredient, also as a formulated composition, is generally between about 0.005 and about 15 kg/ha, preferably between about 0.01 and about 2 kg/ha. Therefore, the rates and concentrations of the formulated compositions may vary according to the method of application and the nature of the compositions and use thereof. Generally speaking, the compositions for application to control arthropod, plant nematode, helminth or protozoan pests usually contain from about 0.00001% to about 95%, more particularly from about 0.0005% to about 50% by weight of one or more compounds of general formula(I) or of total active ingredients (that is to say the compound(s) of general formula(I) together with other substances toxic to arthropods and plant nematodes, anthelmintics, anticoccidials, synergists, trace elements and stabilizers). The actual compositions employed and their rate of application will be selected to achieve the desired effect(s) by the farmer, livestock producer, medical or veterinary practitioner, pest control operator or other person skilled in the art.

Solid and liquid compositions for application topically to animals, timber, stored products or household goods usually contain from about 0.00005% to about 90%, more particularly from about 0.001% to about 10%, by weight of one or more compounds of general formula(I). For administration to animals orally or parenterally, including percutaneously solid and liquid compositions, these normally contain from about 0.1% to about 90% by weight of one or more compounds of general formula(I). Medicated feedstuffs normally contain from about 0.001% to about 3% by weight of one or more compounds of general formula(I). Concentrates and supplements for mixing with feedstuffs normally contain from about 5% to about 90%, preferably from about 5% to about 50%, by weight of one or more compounds of general formula(I). Mineral salt licks normally contain from about 0.1% to about 10% by weight of one or more compounds of general formula(I).

Dusts and liquid compositions for application to livestock, persons, goods, premises or outdoor areas may contain from about 0.0001% to about 15%, more especially from about 0.005% to about 2.0%, by weight, of one or more compounds of general formula(I). Suitable concentrations in treated waters are between about 0.0001 ppm and about 20 ppm, more particularly about 0.001 ppm to about 5.0 ppm. of one or more compounds of general formula(I) and may be used therapeutically in fish farming with appropriate exposure times. Edible baits may contain from about 0.01% to about 5%, preferably from about 0.01% to about 1.0%, by weight, of one or more compounds of general formula(I).

When administered to vertebrates parenterally, orally or by percutaneous or other means, the dosage of compounds of general formula(I) will depend upon the species, age, and health of the vertebrate and upon the nature and degree of its actual or potential infestation by arthropod, helminth or protozoan pests. A single dose of about 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily doses required over a period of months may be combined and administered to animals on a single occasion.

The following composition EXAMPLES 17-28 illustrate compositions for use against arthropods, especially insects, plant nematodes, and helminth or protozoan pests which comprise, as active ingredient, compounds of general formula (I), especially compounds according to formula (II) or (III), such as those described in preparative EXAMPLES 1 to 15. The compositions described in EXAMPLES 17 to 22 can each be diluted in water to give a sprayable composition at concentrations suitable for use in the field. Generic chemical descriptions of the ingredients (for which all of the following percentages are in weight percent), used in the composition EXAMPLES 17-28 exemplified below, are as follows:

| Trade Name | Chemical Description |
| --- | --- |
| Ethylan BCP | Nonylphenol ethylene oxide condensate |

-continued

| Trade Name | Chemical Description |
|---|---|
| Sorprophor BSU | Tristyrylphenol ethylene oxide condensate |
| Arylan CA | A 70% w/v solution of calcium dodecylbenzenesulfonate |
| Solvesso 150 | Light $C_{10}$ aromatic solvent |
| Arylan S | Sodium dodecylbenzenesulfonate |
| Darvan No2 | Sodium lignosulphonate |
| Celite PF | Synthetic magnesium silicate carrier |
| Sopropon T36 | Sodium salts of polycarboxylic acids |
| Rhodigel 23 | Polysaccharide xanthan gum |
| Bentone 38 | Organic derivative of magnesium montmorillonite |
| Aerosil | Microfine silicon dioxide |

EXAMPLE 17

A water soluble concentrate is prepared with the composition as follows:
Active ingredient: 7%
Ethylan BCP: 10%
N-methylpyrrolidone: 83%

To a solution of Ethylan BCP dissolved in a portion of N-methylpyrrolidone is added the active ingredient with heating and stirring until dissolved. The resulting solution is made up to volume with the remainder of the solvent.

EXAMPLE 18

An emulsifiable concentrate (EC) is prepared with the composition as follows:
Active ingredient: 7%
Soprophor BSU: 4%
Arylan CA: 4%
N-methylpyrrolidone: 50%
Solvesso 150: 35%

The first three components are dissolved in N-methylpyrrolidone and to this is then added the Solvesso 150 to give the final volume.

EXAMPLE 19

A wettable powder (WP) is prepared with the composition as follows:
Active ingredient: 40%
Arylan S: 2%
Darvan No2: 5%
Celite PF: 53%

The ingredients are mixed and ground in a hammermill to a powder with a particle size of less than 50 microns.

EXAMPLE 20

An aqueous-flowable formulation is prepared with the composition as follows:
Active ingredient: 40.00%
Ethylan BCP: 1.00%
Sopropon T360: 0.20%
Ethylene glycol: 5.00%
Rhodigel 230: 0.15%
Water: 53.65%

The ingredients are intimately mixed and are ground in a bead mill until a mean particle size of less than 3 microns is obtained.

EXAMPLE 21

An emulsifiable suspension concentrate is prepared with the composition as follows:
Active ingredient: 30%
Ethylan BCP: 10.0%
Bentone 38: 0.5%
Solvesso 150: 59.5%

The ingredients are intimately mixed and ground in a beadmill until a mean particle size of less than 3 microns is obtained.

EXAMPLE 22

A water dispersible granule is prepared with the composition as follows:
Active ingredient: 30%
Darvan No 2: 15%
Arylan S: 8%
Celite PF: 47%

The ingredients are mixed, micronized in a fluid-energy mill and then granulated in a rotating pelletizer by spraying with water (up to 10%). The resulting granules are dried in a fluid-bed drier to remove excess water.

EXAMPLE 23

A dusting powder is prepared with the composition as follows:
Active ingredient: 1 to 10%
Talc powder-superfine: 99 to 90%

The ingredients are intimately mixed and further ground as necessary to achieve a fine powder. This powder may be applied to a locus of arthropod infestation, for example refuse dumps, stored products or household goods or animals infested by, or at risk of infestation by, arthropods to control the arthropods by oral ingestion. Suitable means for distributing the dusting powder to the locus of arthropod infestation include mechanical blowers, handshakers and livestock self treatment devices.

EXAMPLE 24

An edible bait is prepared with the composition as follows:
Active ingredient: 0.1 to 1.0%
Wheat flour: 80%
Molasses: 19.9 to 19%

The ingredients are intimately mixed and formed as required into a bait form. This edible bait may be distributed at a locus, for example domestic and industrial premises, e.g. kitchens hospitals or stores, or outdoor areas, infested by arthropods, for example ants, locusts, cockroaches and flies, to control the arthropods by oral ingestion.

EXAMPLE 25

A solution formulation is prepared with a composition as follows:
Active ingredient: 15%
Dimethyl sulfoxide: 85%

The active ingredient is dissolved in dimethyl sulfoxide with mixing and or heating as required. This solution may be applied to domestic animals infested by arthropods, percutaneously as a pour-on application or, after sterilization by filtration through a polytetrafluoroethylene membrane (0.22 micrometer pore size), by parenteral injection, at a rate of application of from 1.2 to 12 ml of solution per 100 kg of animal body weight.

EXAMPLE 26

A wettable powder is prepared with the composition as follows:
Active ingredient: 50%
Ethylan BCP: 5%

Aerosil: 5%

Celite PF: 40% ·

The Ethylan BCP is absorbed onto the Aerosil which is then mixed with the other ingredients and ground in a hammer-mill to give a wettable powder, which may be diluted with water to a concentration of from 0.001% to 2% by weight of the active compound and applied to a locus of infestation by arthropods, for example dipterous larvae, or plant nematodes by spraying, or to domestic animals infested by, or at risk of infection by, arthropods, helminths or protozoa, by spraying or dipping, or by oral administration in drinking water, to control the arthropods, helminths or protozoa.

EXAMPLE 27

A slow release bolus composition is formed from granules containing the following components in varying percentages (similar to those described for the previous compositions) depending upon need:

Active ingredient

Density agent

Slow-release agent

Binder

The intimately mixed ingredients are formed into granules which are compressed into a bolus with a specific gravity of 2 or more. This can be administered orally to ruminant domestic animals for retention within the reticulo-rumen to give a continual slow release of active compound over an extended period of time to control infestation of the ruminant domestic animals by arthropods, helminths or protozoa.

EXAMPLE 28

A slow release composition in the form of granules, pellets, brickettes and the like can be prepared with compositions as follows:

Active ingredient: 0.5 to 25%

Polyvinyl chloride: 75 to 99.5%

Dioctyl phthalate (plasticizer): catalytic amount

The components are blended and then formed into suitable shapes by melt-extrusion or molding. These compositions are useful, for example, for addition to standing water or for fabrication into collars or eartags for attachment to domestic animals to control pests by slow release.

While the present invention has been set forth in specific and illustrative details and described with preferred particularity, it is susceptible to changes, modifications and alternations, obvious to one of ordinary skill in the art, without departing from the scope and spirit of the invention, which is defined by the claims appended hereto.

What we claim is:

1. A compound of formula 14

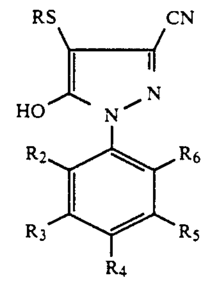

14 wherein:

R is selected from unsubstituted $C_1$ to $C_4$ alkyl or $C_1$ to $C_4$ alkyl substituted by one or more halogen atoms, which are the same or different, up to full substitution;

$R_2$, $R_3$, $R_5$, and $R_6$ are individually a hydrogen atom or a halogen atom;

$R_4$ is selected from a halogen atom or a $C_1$ to $C_4$ straight chain or branched chain alkyl, alkoxy, alkylthio, alkylsulfinyl or alkylsulfonyl group, which group is unsubstituted or substituted by one or more halogen atoms which are the same or different.

2. The compound of claim 1 wherein:

R is $C_1$ to $C_4$ alkyl fully substituted by halogen atoms which are the same or different;

$R_3$ and $R_5$ are each a hydrogen atom;

$R_4$ is selected from a halogen atom, $CF_3$, $OCF_3$, $SCF_3$, $SOCF_3$, $SO_2CF_3$, $OCHF_2$ or $C_1$ to $C_4$ alkyl; and $R_6$ is a halogen atom.

3. The compound of claim 2 wherein:

R is methyl fully substituted by halogen atoms which are the same or different;

$R_2$ and $R_6$ are each a halogen atom; and $R_4$ is $CF_3$.

4. The compound of claim 3 wherein:

R is selected from $CF_3$, $CCl_2F$ or $CClF_2$;

$R_2$ and $R_6$ are each a chlorine atom.

* * * * *

UNITED STATES PATENT AND TRADEMARK OFFICE
CERTIFICATE OF CORRECTION

PATENT NO. : 5,047,550

DATED : September 10, 1991

INVENTOR(S) : D'Silva and Pennicard

It is certified that error appears in the above-identified patent and that said Letters Patent is hereby corrected as shown below:

On the cover page of the patent:
    Column 1, line 2, "D'Silva" should read --D'Silva et al --.
    Column 1, line 4, change "Themistocles D.J. D'Silva, Chappel Hill, N.C." to --Themistocles D.J. D'Silva, Chappel Hill, N.C.; Richard G. Pennicard, Dagenham, England";
Column 9, line 1, insert "EXAMPLE 1" above "Preparation of"

Signed and Sealed this

Twenty-third Day of March, 1993

Attest:

STEPHEN G. KUNIN

*Attesting Officer*      Acting Commissioner of Patents and Trademarks